(12) United States Patent
Engel et al.

(10) Patent No.: US 7,172,904 B2
(45) Date of Patent: Feb. 6, 2007

(54) HIGH SENSITIVITY SENSOR FOR TAGGED MAGNETIC BEAD BIOASSAYS

(75) Inventors: Bradley N. Engel, Chandler, AZ (US); Michael Ward, Glendale, AZ (US)

(73) Assignee: Freescale Semiconductor, Inc., Austin, TX (US)

( * ) Notice: Subject to any disclaimer, the term of this patent is extended or adjusted under 35 U.S.C. 154(b) by 645 days.

(21) Appl. No.: 10/209,524

(22) Filed: Jul. 31, 2002

(65) Prior Publication Data

US 2004/0023365 A1 Feb. 5, 2004

(51) Int. Cl.
*G01N 33/558* (2006.01)
(52) U.S. Cl. .............. 436/514; 436/526; 436/528; 422/52; 422/101; 422/236
(58) Field of Classification Search ............. 436/514, 436/526, 528; 422/236, 52, 101; 428/693, 428/694; 365/173
See application file for complete search history.

(56) References Cited

U.S. PATENT DOCUMENTS

| | | | |
|---|---|---|---|
| 5,445,971 A | 8/1995 | Rohr | |
| 5,902,690 A * | 5/1999 | Tracy et al. | 428/814 |
| 5,981,297 A * | 11/1999 | Baselt | 436/514 |
| 6,057,167 A | 5/2000 | Shieh et al. | |
| 6,381,171 B1 * | 4/2002 | Inomata et al. | 365/173 |
| 2002/0060565 A1 | 5/2002 | Tondra | |

OTHER PUBLICATIONS

Edelstein et al, The BARC biosensor applied to the detection of biological warfare agents, 2000, Biosensors & Bioelectronics, 14, 805-813.*
Baselt et al., "A Biosensor Based on Magnetoresistance Technology," Elsevier Science S.A., 1998, XP-002285269, pp. 731-739.
Edelstein et al., The BARC Biosensor Applied to the Detection of Biological Warfare Agents, Elsevier Science S.A., 2000, xp-001069427, pp. 805-813.
Whitman et al., "The BARC Biosensor," 2001 NRL Review, Chemical/Biochemical Research, pp. 99-101.

* cited by examiner

*Primary Examiner*—Long V. Le
*Assistant Examiner*—N Yang
(74) *Attorney, Agent, or Firm*—Keith Witek; Ranjeev Singh

(57) ABSTRACT

The preferred embodiments of the present invention use MRAM technology to detect a shift in the magnetic switching field of a sensor. The shift in the magnetic switching field is caused by the presence of magnetic tagged beads. By measuring the magnitude of the shift in the magnetic field and correlating the magnitude of the shift to the presence of the target molecules, accurate measurements regarding the presence of the target molecules can be made.

19 Claims, 2 Drawing Sheets

HIGH SENSITIVITY SENSOR FOR TAGGED MAGNETIC BEAD BIOASSAYS

TECHNICAL FIELD

The present invention generally relates to magnetoelectronics, and more particularly to a magnetoelectronic field sensor used in bioassays.

BACKGROUND OF THE INVENTION

Binding bioassays such as immunoassays, DNA hybridization assays, and receptor-based assays are widely used as diagnostic tests for a wide range of target molecules. Binding assays exploit the ability of certain molecules, herein referred to as "binding molecules," to specifically bind target molecules. Binding molecules such as antibodies, strands of polynucleic acids (DNA or RNA) and molecular receptors, are capable of selectively "binding" to such potential target molecules as polynucleic acids, enzymes and other proteins, polymers, metal ions, and low molecular weight organic species such as toxins, illicit drugs, and explosives.

In a solid-phase binding assay, binding molecules are attached to a solid substrate, a procedure generally performed by the manufacturer of the assay. These binding molecules are referred to as "capture" molecules. When the user initiates the assay by exposing the solid substrate to a liquid sample, capture molecules immobilize target and/or label molecules on the surface via recognition events.

Through the use of labeled binding molecules, such recognition events can be made to generate a measurable signal and thereby indicate the presence or absence of a target molecule. Various types of binding assays have been devised that use radioactive, fluorescent, chemiluminescent, magnetic and/or enzymatic labels. Depending on the type of assay being performed, labeled binding molecules either bind to immobilized target molecules, i.e., a "sandwich" assay, or compete with target molecules to bind to capture molecules, i.e., a "competitive" assay. After removal of excess label from the sample, the amount of bound label may be measured.

In addition to the typical binding assays described above, new technologies have created additional ways to identify the target molecules in bioassays. In one specific example, certain nanoscale magnetic beads have successfully been utilized to detect the presence of various target molecules in bioassays. In this application, the magnetic beads, typically a magnetite $Fe_2O_3$ bead, are activated or "tagged" with a biochemical coating that selectively bonds with the biomolecule of interest in a given solution. Once tagged in this fashion, the magnetic beads are placed into the solution where they diffuse to a magnetoresistive sensor and attach themselves to a molecule-specific biochemical coating. The presence, or non-presence, of the tagged beads at the magnetoresistive sensor can be measured based upon the magnetic properties of the beads.

The magnetoresistive sensor can detect changes in the Giant Magnetoresistance (GMR) that is directly related to the influence of the fringing magnetic fields emanating from the beads that are attached to the biochemical coating in relatively close proximity to the magnetoresistive sensor. These magnetite beads are typically about 1–2 micrometers in diameter. These relatively large beads are necessary, given the relatively low sensitivity of the GMR sensor. It should be noted that larger beads can be used to enhance the signal, but larger beads will also tend to produce non-specific binding. Non-specific binding reduces both sensitivity and selectivity and typically increases as the beads increase in size. In addition, several target molecules may be required to adequately bind a larger bead and this may also reduce sensitivity since the presence of a single bead does not indicate the presence of a single target molecule unless it can be bound to only one target molecule.

While the use of magnetic beads to detect target molecules in a solution has been successfully demonstrated, certain practical implementation details have suggested probable limitations on the current technology. For example, the GMR sensor sensitivity is somewhat limited and, accordingly, may limit the ability of the sensor to detect relatively low levels of target molecules in a given solution. The GMR sensor sensitivity is a function of GMR magnitude (maximum resistance change) and the magnetic field response (slope of the magnetic resistance associated with the magnetic field). Presently known GMR sensors have demonstrated a sensitivity of approximately 1-microvolt signal for a single bead. Accordingly, it is possible that relatively small amounts of a target molecule in a solution remain undetectable using the presently known GMR sensors.

In view of the foregoing, it should be appreciated that it would be desirable to enhance the accuracy and sensitivity of bioassays performed using magnetic labels. In addition, it would be desirable to provide new methods and techniques for fabricating sensors without requiring the addition of new and costly procedures. Furthermore, additional desirable features will become apparent to those skilled in the art from the drawings, foregoing background of the invention, following detailed description of the drawings, appended claims, and abstract of the invention.

BRIEF DESCRIPTION OF THE DRAWINGS

The present invention will hereinafter be described in conjunction with the appended drawing figures, wherein like numerals denote like elements, and.

DETAILED DESCRIPTION OF THE DRAWINGS

Typically, a magnetic element, such as a Magnetoresistive Random Access Memory (MRAM) element, has a structure that includes ferromagnetic layers separated by at least one non-magnetic layer. Information is stored as directions of magnetization vectors in the magnetic layers. Magnetic vectors in one magnetic layer, for instance, are magnetically fixed or pinned, while the magnetization direction of the other magnetic layer is free to switch between the same and opposite directions that are called "parallel" and "antiparallel" states, respectively. In response to parallel and antiparallel states, the magnetic memory element represents two different resistances. The resistance has minimum and maximum values when the magnetization vectors of the two magnetic layers point in substantially the same and opposite directions, respectively.

Accordingly, a detection of change in resistance allows a device, such as an MRAM element, to provide information stored in the magnetic memory element. The difference between the minimum and maximum resistance values, divided by the minimum resistance is known as the magnetoresistance ratio (MR). Additional details regarding MRAM elements can be found in U.S. Pat. No. 6,205,052, which patent is incorporated herein by reference.

Figure 1:
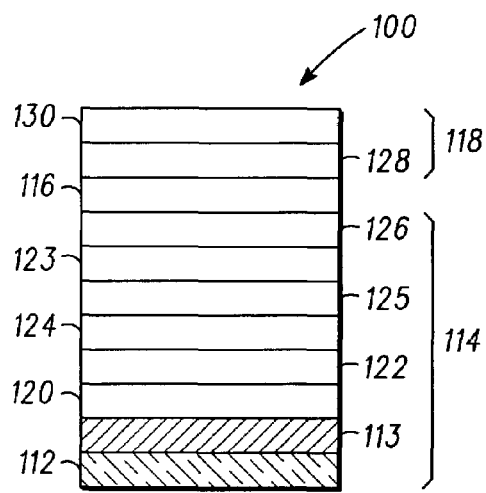
FIG. 1 is a representation of a multi-layer magnetic element suitable for use with a magnetoresistive sensor in accordance with a preferred exemplary embodiment of the present invention.

Referring now to FIG. 1, a magnetic element 100 suitable for use with a preferred exemplary embodiment of the present invention is shown. The structure of magnetic element 100 includes a substrate 112, a first electrode multilayer stack 114, a spacer layer 116, and a second electrode multilayer stack 118. It should be understood that the material composition of magnetic element 100 is dependent upon the type of magnetic element being fabricated and many variations are possible. The specific example given here is for illustration only and those skilled in the art will recognize that other magnetic elements, some with fewer layers and some with more layers, may be utilized without departing from the scope of the present invention.

More particularly, in one embodiment, spacer layer 116 is formed of a dielectric material, and in another embodiment, spacer layer 116 is formed of a conductive material. First electrode multilayer stack 114 and second electrode multilayer stack 118 include one or more ferromagnetic layers. First electrode multilayer stack 114 is formed on a base metal layer 113, which is formed on substrate 112. Base metal layer 113 may be composed of a single metal material or layer or a stack of more than one metal material or layer. First electrode multilayer stack 114 includes a first seed layer 120, deposited on base metal layer 113, a template layer 122, a layer of antiferromagnetic (AF) pinning material 124, and a fixed ferromagnetic layer 126 formed on and exchange coupled with the underlying AF pinning layer 124.

In at least one preferred embodiment of the present invention, seed layer 120 is preferably formed of platinum (Pt), tantalum (Ta), or most preferably tantalum nitride (TaNx). In this embodiment, template layer 122 is fabricated from a conductive material, preferably a nickel, iron, cobalt (NiFeCo) alloy or ruthenium (Ru), is then deposited over seed layer 120.

The combination of seed layer 120 and template layer 122 provide the base for AF pinning layer 124. After the formation of seed layer 120 and template layer 122, AF pinning layer 124 is fabricated from a conductive material, such as an iridium manganese (IrMn) alloy. Ferromagnetic layers 125 and 126 are described as fixed, or pinned, in that the magnetic moment for these layers is prevented from rotation in the presence of an externally applied magnetic field.

In the most preferred embodiments of the present invention, ferromagnetic layers 125 and 126 are separated by coupling layer 123. Coupling layer 123 is most preferably comprised of ruthenium (Ru), rhodium (Rh), osmium (Os), copper (Cu) or the like. Combined with ferromagnetic layers 125 and 126, coupling layer 123 creates a synthetic antiferromagnet (SAF) free layer. The antiferromagnetic coupling provided through layer 123 makes magnetic element 100 more stable in applied magnetic fields.

Second electrode stack 118 includes a free ferromagnetic layer 128 and a protective contact layer 130. The magnetic moment of the free ferromagnetic layer 128 is not fixed, or pinned, by exchange coupling, and is therefore free to rotate in the presence of an applied magnetic field.

It should be understood that a reversed, or flipped, structure is also anticipated by this disclosure. More particularly, it is anticipated that the disclosed magnetic element can be formed to include a top fixed, or pinned layer, and thus be described as a top pinned structure.

Figure 2:
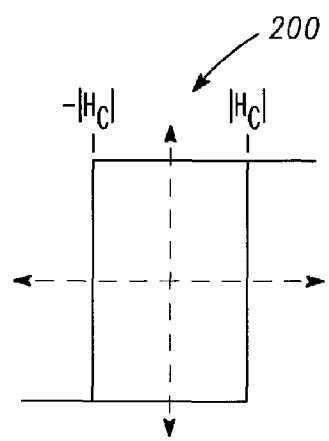
FIG. 2 is a hysteresis curve for the baseline magnetic switching field of a magnetic element according to a preferred exemplary embodiment of the present invention.

Referring now to FIG. 2, a hysteresis curve 200 for a typical MRAM element is depicted. As shown in FIG. 2, curve 200 is substantially rectangular in shape. The points labeled $-|H_C|$ and $|H_C|$ represent the boundaries for the switching of the state of the MRAM element. As shown in FIG. 2, the curve is centered about the X and Y axes.

Figure 3:
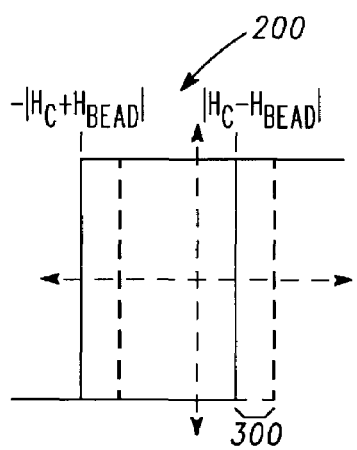
FIG. 3 is the hysteresis curve of FIG. 1 in the presence of an altered magnetic switching field.

Referring now to FIG. 3, hysteresis curve 200 of FIG. 2 is shown after the introduction of some number of magnetic beads to the magnetoresistive sensor employing the MRAM element. As shown in FIG. 3, when the magnetic beads bind to the magnetoresistive sensor, hysteresis curve 200 shifts by a distance 300, due to the fringe magnetic field associated with the magnetic beads captured at the magnetoresistive sensor. As shown in FIG. 3, points labeled $-|H_C+H_{BEAD}|$ and $|H_C-H_{BEAD}|$ represent the new boundaries for the switching of the magnetic state of the MRAM element, after the introduction of the magnetic beads. Distance 300 represents the change in the magnetic switching field due to the presence of the magnetic beads. The shift is caused by the presence of the magnetic beads localized near one end of the sensor.

The shift associated with distance 300 in hysteresis curve 200 can be correlated to the presence of the magnetic beads that are bound to the target molecules, which have been bound to the magnetoresistive sensor. Accordingly, the presence of the magnetic beads corresponds to the presence of the target molecule and the amount of the shift in hysteresis curve 200 can be used to determine the amount of target molecules present. In certain circumstances, in addition to exhibiting the shift described above, the shape of hysteresis curve 200 may also change.

Figure 4:
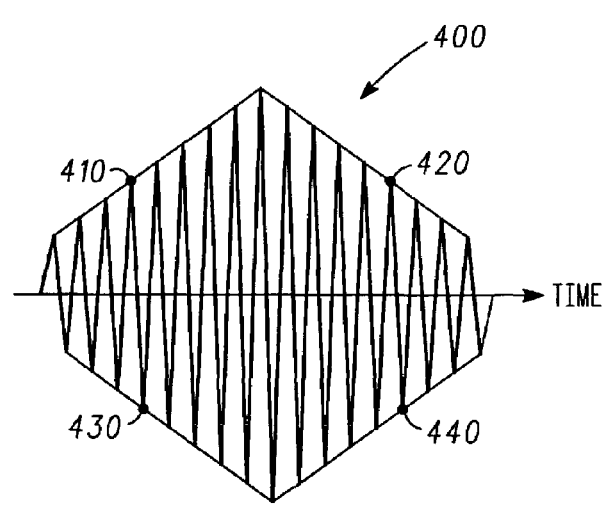
FIG. 4 is a wave diagram for a biomolecule detection method according to a preferred exemplary embodiment of the present invention.

Referring now to FIG. 4, an amplitude diagram 400 for the switching current of an MRAM element incorporated into a magnetoresistive sensor according to a preferred exemplary embodiment of the present invention is shown. Switching points 410, 420, 430, and 440 represent the current levels and the points in time for the state of the MRAM element to switch from the "parallel" state to the "antiparallel" state or vice versa. It should be noted that while the current embodiment depicts a triangular modulation scheme for the current supplied to the MRAM element, other modulation schemes known to those skilled in the art may also be employed. As shown in FIG. 4, switching points 410, 420, 430, and 440 depict a certain symmetry.

Figure 5:
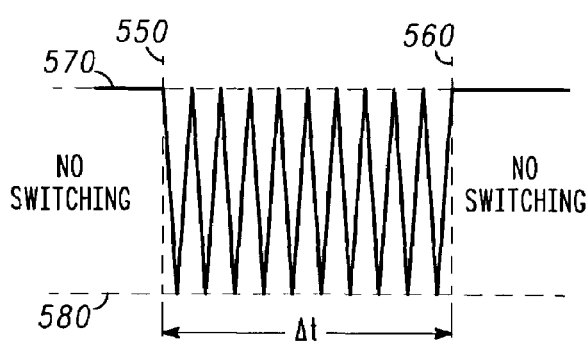
FIG. 5 is a switching diagram for an MRAM element according to a preferred exemplary embodiment of the present invention.

Referring now to FIG. 5, the switching activity of an MRAM element operating without the presence of a magnetic bead is depicted as a function of resistance over time.

Prior to reaching switching point 450, the measured resistance of the MRAM element is stable and no switching takes place. However, as the amplitude is increased, it will eventually reach the threshold for necessary to change the state of the MRAM element. When the amplitude ramp reaches that point, as represented by switching point 450, the MRAM element will begin to alternatively switch from a high resistance level 470 (first resistance level) to a low resistance level 480 (second resistance level) and back again at the same frequency as the modulation frequency.

Eventually, as the amplitude ramp is decreased, the magnetic switching field will once again decrease below the switching threshold, as represented by switching point 460, and the MRAM element will stop switching and return to a stable measured resistance level. The time between the point where the MRAM element starts switching and the point where the MRAM element stops switching can be designated as $\Delta t$.

Figure 6:
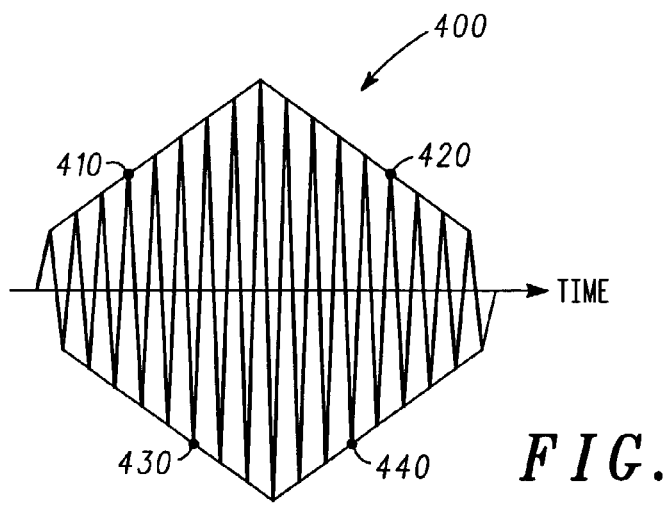
FIG. 6 is the wave diagram of FIG. 4 after the introduction of a biomolecule.

Referring now to FIG. 6, amplitude diagram 400 of FIG. 4 is shown with the addition of a number of magnetic beads attached to the magnetoresistive sensor. As shown in FIG. 5, switching points 410, 420, 430, and 440 are no longer symmetrical in the way depicted in FIG. 4. The movement of switching points 410, 420, 430, and 440 represents a change in time for the MRAM element to switch from the "parallel" state to the "antiparallel" state or vice versa. This change represents the shift depicted in FIGS. 2 and 3 due to the presence of the magnetic beads. In this case, the time relation of the switch event to the amplitude ramp is the measure of the field shift and represents the detection of the magnetic beads. By calibrating the modulation of the amplitude current, a correlation can be made to the number of magnetic beads detected.

Figure 7:
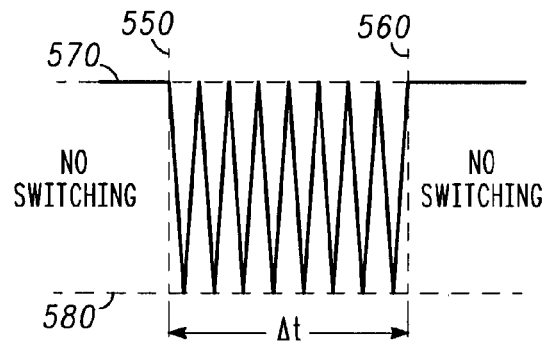
FIG. 7 is the switching diagram of FIG. 5 when detecting the presence of a magnetic bead in accordance with a preferred exemplary embodiment of the present invention.

Referring now to FIG. 7, the switching activity of the MRAM element of FIG. 5, in the presence of one or more magnetic beads is depicted as a function of resistance over time. Prior to reaching switching point 450, the measured resistance of the MRAM element is stable and no switching takes place. However, as the amplitude is increased, it will eventually reach the threshold for necessary to change the state of the MRAM element. When the amplitude ramp reaches that point, as represented by switching point 450, the MRAM element will begin to alternatively switch from a high resistance level 470 to a low resistance level 480 and back again at the same frequency as the modulation frequency.

Eventually, as the amplitude is decreased, the magnetic switching field will once again decrease below the switching threshold, as represented by switching point 460, and the MRAM element will stop switching and return to a stable measured resistance level. The time between the point where the MRAM element starts switching and the point where the MRAM element stops switching can be designated as $\Delta t$. As can be seen by referring to both FIG. 5 and FIG. 7, $\Delta t$ is smaller in the presence of one or more magnetic beads. This difference can be correlated to provide a measurement for the number of beads present and, by extension, the amount of target molecule present in the sample as well. The variance in $\Delta t$ will be determined by the number of magnetic beads attached to the sensor device containing the MRAM element. Accordingly, by implementing the methodologies described herein, the sensor circuit incorporating the MRAM element need only be able to detect the onset and cessation of the switching of the MRAM element relative to the amplitude ramp of the modulation current.

Figure 8:
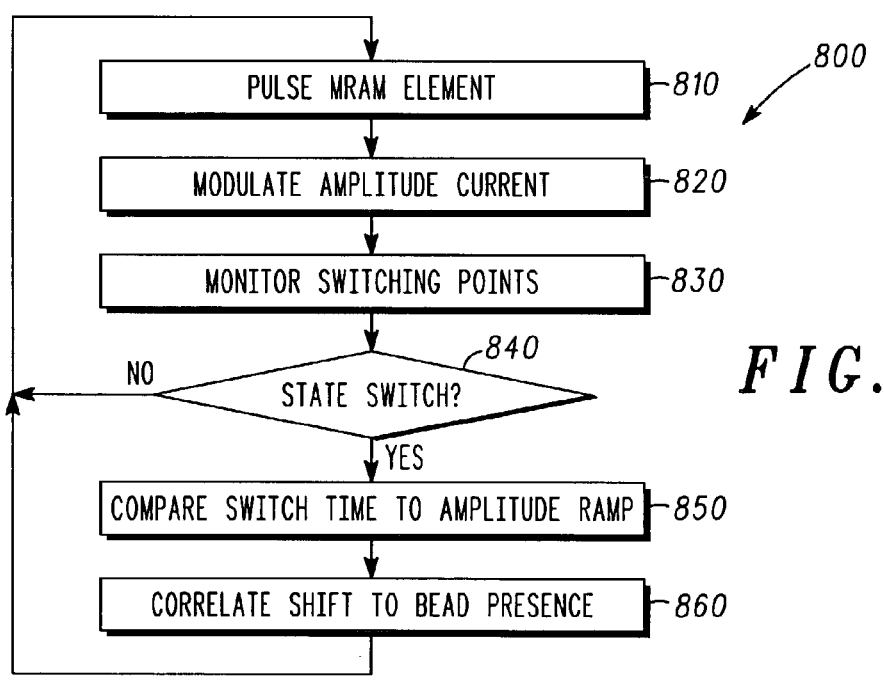
FIG. 8 is a flow chart of a method for detecting biomolecules according to a preferred embodiment of the present invention.

Referring now to FIG. 8, a method 800 for using an MRAM element to detect biomolecules according to a preferred exemplary embodiment of the present invention is disclosed. As shown in FIG. 8, the MRAM element is continuously pulsed with an alternating current at a relatively high frequency (step 810). The pulsing is accomplished by providing the pulse current to a plurality of programming conductors associated with the MRAM element. The programming conductors are current lines that produce the applied magnetic switching field for switching the MRAM element. The supplied pulse current is amplitude modulated at a frequency rate that is lower than the frequency of the pulse current (step 820). During the modulation cycle, the MRAM element is monitored for any change in state (step 830). The amplitude of the pulse current is gradually changed until the state of the MRAM element changes. As previously mentioned, the MRAM element state change will be a toggling between a high resistance level and a low resistance level. The state of the MRAM element can be determined by measuring the resistance of the MRAM element.

If the state of the MRAM element has not switched (step 840 equal "NO"), then the method returns to step 810 and continues as before, gradually changing the amplitude current supplied to the MRAM device. Eventually, the switching threshold of the MRAM element will be reached, and the MRAM element will repeatedly switch back and forth from the "parallel" state to the "antiparallel" state (step 840 equal "YES"). By comparing the time at the point of the state switch to the amplitude ramp (step 850), the presence or non-presence of the magnetic beads can be determined (step 860). Whenever a magnetic bead is captured by the sensor, a shift in the switching transition time will be manifest. The more beads captured by the sensor, the greater the shift in the switching point for the MRAM element.

To provide a better signal-to-noise ratio (SNR) for the magnetoresistive sensor, it may be desirable to operate the switching current at a relatively high frequency and then perform signal averaging. Additionally, in order to isolate the sensor from external magnetic sources, it may also be desirable to shield the sensor housing containing the MRAM element and fluid sample.

In order to take full advantage of the sensitivity of the MRAM elements, it is desirable to locate the selective chemistries for attachment and detection as close as possible to the end of the MRAM bit. Using self-assembling alkanethiols and photolithography techniques it is possible to place the desired selective chemistries in close proximity to one end of the MRAM bit. By placing these chemistries at just one end of the structure, changes in the magnetic field resulting from bead attachment are maximized.

One possible methodology for creating the asymmetrical coating begins by sputtering the entire surface with a 10–100 angstrom layer of gold. Long chain alkanethiols (>16 carbon chain) are then self-assembled on the sputtered gold surface using standard process techniques. Portions of the resulting monolayer, covering one side of each bit, are then removed using a photo mask and UV light. The exposed portions can be replaced with alkanethiols from a second solution that have a desired functionality at the distal end, thereby creating an asymmetrical monolayer. Finally, probes that react with the desired functionality can be added using a commercial arrayer or other probe-spotting device. It should be noted that a typical 100-micron spot deposited by a typical arrayer would attach probes of the same type to many MRAM elements. The signals generated by these discrete elements could then be averaged together to add selectivity and specificity to an assay.

In addition to providing a convenient method for creating the selective chemistries of the present invention, the previously described alkanethiol monolayer is also useful for providing a thin (<10 nm) electrically insulating barrier to protect against certain corrosive, conducting analyte solutions. The insulting properties of the monolayer can be adjusted by increasing the length of the alkyl chains and a longer chain molecule is desirable for better insulation.

With the asymmetrical localized areas of activated sensor material, the magnetic beads will diffuse through the sample surrounding the sensor and some number of magnetic beads, attached to target molecules, will become attached to the surface of the sensor at the areas where the activated sensor material has been deposited. The asymmetrical nature of the bead attachment will influence the magnetic switching field as described above.

From the foregoing description, it should be appreciated that the methods and techniques disclosed herein present significant benefits that would be apparent to one skilled in the art. Furthermore, while multiple embodiments have been presented in the foregoing descriptions, it should be appreciated that a vast number of variations in the embodiments exist. Lastly, it should be appreciated that these embodiments are preferred exemplary embodiments only, and are not intended to limit the scope, applicability, or configuration of the invention in any way. Rather, the foregoing detailed descriptions provide those skilled in the art with a convenient road map for implementing the preferred exemplary embodiments of the invention. It being understood that various changes may be made in the function and arrangement of elements described in the exemplary preferred embodiments without departing from the spirit and scope of the invention as set forth in the appended claims.

The invention claimed is:

1. A method of detecting at least one target molecule using a magnetoresistive random access memory (MRAM) element, wherein the MRAM element may be in a first state or a second state, comprising the steps of:
    monitoring at least one switching point in time from the first state to the second state, in response to the application of a switching current signal to the MRAM element;
    attaching at least one magnetic bead to a magnetoresistive sensor incorporating said MRAM element;
    detecting a shift in the at least one switching point in time from the first state to the second state; and
    using said shift to identify the presence of at least one target molecule, said target molecule being attached to said at least one magnetic bead.

2. The method of claim 1, wherein the switching current signal is pulsed at a predetermined frequency.

3. The method of claim 1, wherein the switching current signal is provided to a plurality of programming conductors associated with the MRAM element.

4. The method of claim 3, wherein the plurality of programming conductors are current lines that produce a magnetic switching field for switching the MRAM element from the first state to the second state.

5. The method of claim 1, wherein said step of detecting the at least one target module further comprises the steps of:
    calculating a first differential between the at least one switching point in time and a second switching point in time; and
    calculating a second differential between a third switching point in time and a fourth switching point in time.

6. The method of claim 1 further comprising modulating said switching current signal using amplitude modulation.

7. The method of claim 1 further comprising the step of shielding said MRAM element from at least one external magnetic field.

8. A method of detecting at least one target molecule using a magnetoresistive random access memory (MRAM) element, wherein the MRAM element may be in a first state or a second state, comprising the steps of:
    monitoring at least one switching point in time from the first state to the second state, in response to the application of a switching current signal to the MRAM element, wherein the switching signal has a predetermined frequency;
    attaching at least one magnetic bead to a magnetoresistive sensor incorporating said MRAM element;
    detecting a shift in the at least one switching point in time from the first state to the second state; and
    using said shift to identify the presence of at least one target molecule, said target molecule being attached to said at least one magnetic bead.

9. The method of claim 8, wherein the switching current signal is provided to a plurality of programming conductors associated with the MRAM element.

10. The method of claim 9, wherein the plurality of programming conductors are current lines that produce a magnetic switching field for switching the MRAM element from the first state to the second state.

11. The method of claim 8, wherein said step of detecting the at least one target module further comprises the steps of:
    calculating a first differential between the at least one switching point in time and a second switching point in time; and
    calculating a second differential between a third switching point in time and a fourth switching point in time.

12. The method of claim 8 further comprising modulating said switching current signal using amplitude modulation.

13. The method of claim 8 further comprising the step of shielding said MRAM element from at least one external magnetic field.

14. A method of detecting at least one target molecule using a magnetoresistive random access memory (MRAM) element, wherein the MRAM element may be in a first state or a second state, comprising the steps of:
    monitoring at least one switching point in time from the first state to the second state, in response to the application of a switching current signal to the MRAM element;
    attaching at least one magnetic bead to a magnetoresistive sensor incorporating said MRAM element;
    detecting a shift in the at least one switching point in time from the first state to the second state;
    using said shift to identify the presence of at least one target molecule, said target molecule being attached to said at least one magnetic bead; and
    performing signal averaging to increase the signal-to-noise ratio.

15. The method of claim 14, wherein the switching current signal is pulsed at a predetermined frequency.

16. The method of claim 14, wherein the switching current signal is provided to a plurality of programming conductors associated with the MRAM element.

17. The method of claim 16, wherein the plurality of programming conductors are current lines that produce a magnetic switching field for switching the MRAM element from the first state to the second state.

18. The method of claim 14, wherein said step of detecting the at least one target module farther comprises the steps of:

calculating a first differential between the at least one switching point in time and a second switching point in time; and calculating a second differential between a third switching point in time and a fourth switching point in time.

19. The method of claim 14 further comprising modulating said switching current signal using amplitude modulation.

* * * * *